(12) United States Patent
Kataoka et al.

(10) Patent No.: US 11,311,508 B2
(45) Date of Patent: Apr. 26, 2022

(54) MEDICINAL COMPOSITION FOR PREVENTING OR TREATING SECONDARY HYPERPARATHYROIDISM UNDER MAINTENANCE DIALYSIS

(71) Applicant: EA Pharma Co., Ltd., Chuo-ku (JP)

(72) Inventors: Daisuke Kataoka, Tokyo (JP); Kazuo Kuyama, Aichi (JP); Kenji Asano, Aichi (JP); Hirotaka Wagatsuma, Kanagawa (JP); Atsushi Tsuruta, Kanagawa (JP); Toshiyuki Takanohashi, Kanagawa (JP)

(73) Assignee: EA Pharma Co., Ltd., Chuo-ku (JP)

( * ) Notice: Subject to any disclaimer, the term of this patent is extended or adjusted under 35 U.S.C. 154(b) by 0 days.

(21) Appl. No.: 16/954,884

(22) PCT Filed: Dec. 19, 2018

(86) PCT No.: PCT/JP2018/046679
§ 371 (c)(1),
(2) Date: Jun. 17, 2020

(87) PCT Pub. No.: WO2019/124411
PCT Pub. Date: Jun. 27, 2019

(65) Prior Publication Data
US 2020/0397731 A1 Dec. 24, 2020

(30) Foreign Application Priority Data
Dec. 20, 2017 (JP) .............................. JP2017-244149

(51) Int. Cl.
*A61K 31/198* (2006.01)
*A61P 5/18* (2006.01)
*A61K 9/00* (2006.01)

(52) U.S. Cl.
CPC .......... *A61K 31/198* (2013.01); *A61K 9/0019* (2013.01); *A61P 5/18* (2018.01)

(58) Field of Classification Search
None
See application file for complete search history.

(56) References Cited

U.S. PATENT DOCUMENTS

| 8,946,474 B2 | 2/2015 | Ebdrup et al. |
| 2013/0072491 A1 | 3/2013 | Yasuda et al. |
| 2013/0143846 A1 | 6/2013 | Ebdrup et al. |
| 2013/0237702 A1 | 9/2013 | Sugiki et al. |
| 2015/0366969 A1 | 12/2015 | Shikamura et al. |
| 2016/0101091 A1 | 4/2016 | Sugiki et al. |
| 2018/0079715 A1 | 3/2018 | Okado et al. |

FOREIGN PATENT DOCUMENTS

| JP | 2013-63971 | * | 4/2013 | ........... A61K 31/185 |
| JP | 2013-063971 | * | 4/2013 | ........... C07C 275/42 |
| JP | 2013-63971 A | | 4/2013 | |
| JP | 5423854 B2 | | 2/2014 | |
| RU | 2599788 C2 | | 8/2014 | |
| WO | WO 2011/108690 A1 | | 9/2011 | |
| WO | WO2011/108724 A1 | | 9/2011 | |
| WO | WO 2012/000499 A | | 1/2012 | |
| WO | WO2014/119643 A1 | | 8/2014 | |
| WO | WO2016/194881 A1 | | 12/2016 | |

OTHER PUBLICATIONS

Notice of Reasons for Rejection dated Jan. 15, 2019 in Japanese Patent Application No. 2018-236868 (with English machine translation), 7 pages.

Written Opinion dated Jan. 22, 2019 in PCT/JP2018/046679 (with English language translation), 10 pages.

Nobuo Nagano, et al., "Pharmacological and clinical profiles of calcimimetics for secondary hyperparathyroidism in chronic kidney disease patients on dialysis (cinacalcet hydrochloride, REGPARA®)," Folia Pharmacol. Jpn., vol. 132, 2008, 13 pages (with partial English language translation).

Masafumi Fukagawa, et al., "Cinacalcet (KRN1493) effectively decreases the serum intact PTH level with favourable control of the serum phosphorus and calcium levels in Japanese dialysis patients," Nephrol Dial Transplant, vol. 23, 2008, pp. 328-325.

"REGPARA® tablets, Pharmaceutical Product Interview Form," Kyowa Hakko Kirin, Apr. 2018, 6 pages (with partial English language translation).

Yekaterina Gincherman, et al., "Assessment of adherence to cinacalcet by prescription refill rates in hemodialysis patients," Hemodialysis International, vol. 14, 2010, pp. 68-72.

Toshiyuki Date, "Side effects of Cinacalcet and Countermeasures Thereof," Dialysis Treatment Next IX, 2009, 16 pages (with partial English language translation).

"PARSABIV® Pharmaceutical Product Interview Form," Ono Pharmaceutical Co., Ltd., Dec. 2017, 15 pages (with partial English language translation).

Keitaro Yokoyama, et al., "A Single- and Multiple-Dose, Multicenter Study of Etelcalcetide in Japanese Hemodialysis Patients with Secondary Hyperparathyroidism," Kidney International Reports, vol. 2, 2017, pp. 634-644.

(Continued)

*Primary Examiner* — Brian Gulledge
(74) *Attorney, Agent, or Firm* — Oblon, McClelland, Maier & Neustadt, L.L.P.

(57) ABSTRACT

A medicinal composition for preventing or treating secondary hyperparathyroidism under maintenance dialysis, said medicinal composition comprising 3-{[(2S)-2-amino-2-carboxyethyl]carmaboylamino}-5-chloro-4-methylbenzenesulfonic acid or a pharmaceutically acceptable salt thereof, or a solvate of the same which is to be administered by a predefined route in a predefined dosage. According to the present invention, it is possible to provide a prophylactic or therapeutic agent for secondary hyperparathyroidism under maintenance dialysis, said agent showing reduced side effects or no significant accumulation. This medicinal agent allows easy administration management and has a high safety compared with conventional products.

15 Claims, 4 Drawing Sheets

(56) References Cited

OTHER PUBLICATIONS

Keitaro Yokoyama, et al., "A 12-week dose-escalating study of etelcalcetide (ONO-5163/AMG 416), a novel intravenous calcimimetic, for secondary hyperparathyroidism in Japanese hemodialysis patients," Clinical Nephrology, vol. 88, No. 2, 2017, pp. 68-78.

Sawsan Ibrahim Kreydiyyeh, et al., "PGE2 exerts dose-dependent opposite effects on net water and chloride absorption from the rat colon," Prostaglandins & other Lipid Mediators, vol. 79, 2006; pp. 43-52.

Noriko Makita, et al., "An acquired hypocalciuric hypercalcemia autoantibody induces allosteric transition among active human Ca-sensing receptor conformations," PNAS, vol. 104, No. 13, Mar. 27, 2007, pp. 5443-5448.

Randolph A. Chen, et al., "Role of the calcium-sensing receptor in parathyroid gland physiology," Am J Physiol Renal Physiol, vol. 286, Jun. 2004, pp. F1005-F1011.

International Search Report dated Jan. 22, 2019 in PCT/JP2018/046679 filed on Dec. 19, 2018, 1 page.

Extended European Search Report dated Sep. 20, 2021 in corresponding European Patent Application No. 18893074.7, 8 pages.

Anonymous: "Dose Adjustment Trial of SK-1403 in Hemodialysis Patients With Secondary Hyperparathyroidism—Tabular View", Clinicaltrials.gov, Jul. 21, 2017, pp. 1-6, XP055839112, Internet Retrieved from the Internet: URL:https://clinicaltrials.gov/ct2/show/record/NCT03226171 [retrieved on Sep. 8, 2021].

Office Action and Search Result dated Nov. 10. 2021 to the corresponding Russian Patent Application No. 2020123405 with English translation.

International Search Report dated Jun. 16, 2020 in PCT/JP2020/015129 filed Apr. 2, 2020 (with English-language translation), 5 pages.

Written Opinion dated Jun. 16, 2020 in PCT/JP2020/015129 filed Apr. 2, 2020 (w/ English-language translation), 12 pages.

Office Action and Search Result issued on Nov. 10. 2021 to the corresponding Russian Patent Application No. 2020123405 with English translation.

* cited by examiner

MEDICINAL COMPOSITION FOR PREVENTING OR TREATING SECONDARY HYPERPARATHYROIDISM UNDER MAINTENANCE DIALYSIS

FIELD OF THE INVENTION

The present invention relates to a medicinal composition for preventing and treating secondary hyperparathyroidism under maintenance dialysis, and a method for treating thereof, and the like, wherein 3-{[(2S)-2-amino-2-carboxyethyl]carbamoylamino}-acid, a pharmaceutically acceptable salt thereof or a solvate thereof is administered with a specific dosage and administration.

BACKGROUND ART

Parathyroid hormone (PTH) produced in the parathyroid cells has effects on the kidney to enhance calcium (Ca) reabsorption and suppresses reabsorption of inorganic phosphorus (P) from the urine. It also enhances production of activated vitamin D, which promotes intestinal Ca absorption. This hormone further has effects on the bone and promotes bone absorption, by which Ca and P homeostasis is maintained in the body. Secretion of PTH is enhanced in response to decrease in Ca, increase in P and decrease in activated vitamin D in the blood.

In cases of chronic kidney disease, as the renal function decreases with pathological progression, P excretion into the urine is decreased and activated vitamin D is decreased due to failure of vitamin D activation, which result in hyperphosphatemia and hypocalcaemia and leads to elevation of PTH secretion. Persistent stimulation of PTH secretion to the parathyroid glands enhances proliferation of the parathyroid cells, and parathyroid hyperplasia causes excessive secretion of PTH, which results in onset and progression of the condition of secondary hyperparathyroidism (SHPT). In particular, SHPT is frequently caused in patient on dialysis, where excessive PTH induces high turnover bone lesions (fibrous osteitis), increasing Ca and P in the blood. This is problematic in that not only quality of life is decreased but also cardiovascular calcification is caused which leads to poor life prognosis (Non-patent document 1: Nobuo NAGANO, Takehisa KAWATA, Michihito WADA, *Pharmacological and clinical profiles of calcimimetics for secondary hyperparathyroidism in chronic kidney disease patients on dialysis (cinacalcet hydrochloride, REGPARA (registered trademark) tablet)*, Folia Pharmacologica Japonica, 2008; 132: 301-308).

While conventional medical treatments for decreasing PTH in the blood employ use of activated vitamin D formulations, their therapeutic effects have been considered insufficient because their administration is limited to the problem of increase in the blood Ca and P concentrations caused by enhancement of the intestinal absorption.

A recently launched oral CaSR activator, cinacalcet hydrochloride (hereinafter, cinacalcet), reduces not only PTH but also Ca and P in the blood by suppressing PTH secretion as when concentration of $Ca^{2+}$ as the endogenous ligand is increased (Non-patent document 2: Fukagawa M et al., KRN1493 study group, *Cinacalcet (KRN1493) effectively decreases the serum intact PTH level with favorable control of the serum phosphorus and calcium levels in Japanese dialysis patients*, Nephrol Dial Transplant. 2008; 23(1):328-35).

Administration of cinacalcet, however, is known to frequently manifest digestive symptoms such as nausea and vomiting, and thus has an issue concerning patients who have to discontinue administration or who cannot increase the dose (Non-patent document 3: REGPARA (registered trademark) tablet, Medicine Interview Form (pp. 1-2: 1. Development History), Kyowa Hakko Kirin (revised in April, 2015), and Non-patent document 4: Gincherman Y et al., *Assessment of adherence to cinacalcet by prescription refill rates in hemodialysis*, Hemodial Int. 2010; 14(1): 68-72). While details of the mechanism involved in the digestive symptoms caused by cinacalcet are unknown, increase in the gastric acid secretion and poor peristaltic movement of the digestive tract by activation of CaSR in the digestive tract are suggested to be some of the possible causes (Non-patent document 5: Toshiyuki DATE, *Side effects of Cinacalcet and Countermeasures Thereof*, Takashi AKIBA, Tadao AKIZAWA (eds.), Dialysis Treatment Next IX, Igakutosho Shuppan, Tokyo, 2009, pp. 123-32).

Moreover, a CaSR agonist, etelcalcetide (N-acetyl-S-[(2R)-2-amino-2-carboxyethylsulfanyl]-D-cysteinyl-D-alanyl-D-arginyl-D-arginyl-D-arginyl-D-alanyl-D-argininamide hydrochloride), was launched under the trade name of PARSABIV (registered trademark) in 2017 as an intravenous formulation having an efficacy and an effect for secondary hyperparathyroidism undergoing hemodialysis. Etelcalcetide, however, has problems such as excessive decrease in the serum Ca concentration, accumulating property and the like, and thus requires regular checking on patient's condition and consideration of treatments such as weight reduction and break from medication, and also requires careful medication management due to side effects such as hypersensitivity reaction and vomiting (Non-patent document 6: PARSABIV (registered trademark), Medicine Interview Form (p. 9: V. Items Relating to Treatment, pp. 47-50: 8. Side effects), Ono Pharmaceutical Co., Ltd., Non-patent document 7: Kidney International Reports (2017) 2, 634-644, and Non-patent document 8: Clinical Nephrology, Vol. 88 No. 2, 2017, 68-78).

In this regard, WO2011/108690 (Patent document 1) and JP 2013-63971 A (Patent document 2) show that (2S)-2-amino-3-{[(3-chloro-2-methyl-5-sulfophenyl)carbamoyl]amino}propanoic acid activates CaSR, while Patent document 2 shows that oral administration of the same to nephrectomized rats decreases PTH.

PRIOR ART DOCUMENTS

Patent Documents

Patent document 1: WO2011/108690
Patent document 2: JP 2013-63971 A

Non-Patent Documents

Non-patent document 1: Folia Pharmacologica Japonica 2008; 132: 301-308
Non-patent document 2: Nephrol Dial Transplant. 2008; 23(1):328-35
Non-patent document 3: REGPARA (registered trademark) tablet, Medicine Interview Form (pp. 1-2: 1. Development History), Kyowa Hakko Kirin (revised in April 2015)
Non-patent document 4: Hemodial Int. 2010; 14(1):68-72
Non-patent document 5: Toshiyuki DATE, Side effects of Cinacalcet and Countermeasures Thereof, Takashi AKIBA, Tadao AKIZAWA (eds.), Dialysis Treatment Next IX, Igakutosho Shuppan, Tokyo, 2009, pp. 123-32

Non-patent document 6: PARSABIV (registered trademark) Medicine Interview Form (p. 9: V. Items Relating to Treatment, pp. 47-50: 8. Side effects), Ono Pharmaceutical Co., Ltd.
Non-patent document 7: Kidney International Reports (2017) 2, 634-644
Non-patent document 8: Clinical Nephrology, Vol. 88 No. 2, 2017, 68-78

SUMMARY OF INVENTION

Problem to be Solved by the Invention

In order to prevent or treat secondary hyperparathyroidism under maintenance dialysis, there has been a demand for a highly convenient and excellent medicinal composition.

Means for Solving Problem

In view of the above-described problems, the present inventors have gone through intensive investigation, and as a result of which found that 3-{[(2S)-2-amino-2-carboxyethyl]carbamoylamino}-5-chloro-4-methylbenzenesulfonic acid (hereinafter, Compound A), a pharmaceutically acceptable salt thereof or a solvate thereof is effective with a specific dosage and administration in preventing or treating secondary hyperparathyroidism under maintenance dialysis, thereby accomplishing the present invention.

[Chemical formula 1]

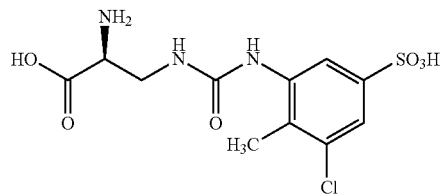

Compound A

Specifically, the present invention comprises, for example, the aspects described below.

A medicinal composition for preventing or treating or a method for treating secondary hyperparathyroidism under maintenance dialysis, wherein 3-{[(2S)-2-amino-2-carboxyethyl]carbamoylamino}-5-chloro-4-methylbenzenesulfonic acid, a pharmaceutically acceptable salt thereof or a solvate thereof is intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg.

A medicinal composition for preventing or treating or a method for treating secondary hyperparathyroidism under maintenance dialysis with reduced side effects, wherein 3-{[(2S)-2-amino-2-carboxyethyl]carbamoylamino}-5-chloro-4-methylbenzenesulfonic acid, a pharmaceutically acceptable salt thereof or a solvate thereof is intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg.

A medicinal composition for preventing or treating or a method for treating secondary hyperparathyroidism under maintenance dialysis without manifesting significant accumulating property, wherein 3-{[(2S)-2-amino-2-carboxyethyl]carbamoylamino}-5-chloro-4-methylbenzenesulfonic acid, a pharmaceutically acceptable salt thereof or a solvate thereof intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg.

A medicinal composition for preventing or treating or a method for treating secondary hyperparathyroidism under maintenance dialysis for long-term administration, wherein 3-{[(2S)-2-amino-2-carboxyethyl]carbamoylamino}-5-chloro-4-methylbenzenesulfonic acid, a pharmaceutically acceptable salt thereof or a solvate thereof is intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg.

The medicinal composition or the therapeutic method according to any one of the above aspects, wherein the end of dialysis means the end of each dialysis session in a dialysis schedule of 3-5 sessions a week.

The medicinal composition or the therapeutic method according to any one of the above aspects, wherein 3-{[(2S)-2-amino-2-carboxyethyl]carbamoylamino}-5-chloro-4-methylbenzenesulfonic acid, a pharmaceutically acceptable salt thereof or a solvate thereof is sodium 3-{[(2S)-2-amino-2-carboxyethyl]carbamoylamino}-5-chloro-4-methylbenzenesulfonate or a solvate thereof.

The medicinal composition or the therapeutic method according to any one of the above aspects, wherein 3-{[(2S)-2-amino-2-carboxyethyl]carbamoylamino}-5-chloro-4-methylbenzenesulfonic acid, a pharmaceutically acceptable salt thereof or a solvate thereof is sodium 3-{[(2S)-2-amino-2-carboxyethyl]carbamoylamino}-5-chloro-4-methylbenzenesulfonate.

In particular, the followings are the preferred aspects.

[1] A medicinal composition for preventing or treating secondary hyperparathyroidism under maintenance dialysis, the composition comprising 3-{[(2S)-2-amino-2-carboxyethyl]carbamoylamino}-5-chloro-4-methylbenzenesulfonic acid, a pharmaceutically acceptable salt thereof or a solvate thereof, wherein the composition is intravenously administered at the end of dialysis with a daily dose of 0.025 mg-0.8 mg for adults.

[2] A medicinal composition for preventing or treating secondary hyperparathyroidism under maintenance dialysis with reduced side effects, the composition comprising 3-{[(2 S)-2-amino-2-carboxyethyl]carbamoylamino}-5-chloro-4-methylbenzenesulfonic acid, a pharmaceutically acceptable salt thereof or a solvate thereof, wherein the composition is intravenously administered at the end of dialysis with a daily dose of 0.025 mg-0.8 mg for adults.

[3] A medicinal composition for preventing or treating secondary hyperparathyroidism under maintenance dialysis without manifesting significant accumulating property, the composition comprising 3-{[(2S)-2-amino-2-carboxyethyl]carbamoylamino}-5-chloro-4-methylbenzenesulfonic acid, a pharmaceutically acceptable salt thereof or a solvate thereof, wherein the composition is intravenously administered at the end of dialysis with a daily dose of 0.025 mg-0.8 mg for adults.

[4] The medicinal composition according to any one of [1]-[3], which is intravenously administered with a daily dose of 0.025-0.4 mg for adults.
[5] The medicinal composition according to any one of [1]-[3], which is intravenously administered at the end of dialysis with a daily dose of 0.05-0.2 mg for adults.
[6] The medicinal composition according to any one of [1]-[5], wherein the end of dialysis means the end of each dialysis session in a dialysis schedule of 3-5 sessions a week.
[7] The medicinal composition according to any one of [1]-[6], wherein 3-{[(2S)-2-amino-2-carboxyethyl]carbamoylamino}-5-chloro-4-methylbenzenesulfonic acid, a pharmaceutically acceptable salt thereof or a solvate thereof is sodium 3-{[(2S)-2-amino-2-carboxyethyl]carbamoylamino}-5-chloro-4-methylbenznesulfonate or a solvate thereof.

Another aspect of the present invention comprises a medicinal composition for preventing or treating or a method for treating secondary hyperparathyroidism under maintenance dialysis, wherein the composition comprises Compound A, a pharmaceutically acceptable salt thereof or a solvate thereof and the composition is intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg to regulate the serum PTH concentration to the normal level.

Furthermore, another aspect of the present invention comprises a medicinal composition for preventing or treating or a method for treating secondary hyperparathyroidism under maintenance dialysis, wherein the composition comprises Compound A, a pharmaceutically acceptable salt thereof or a solvate thereof, and the composition is intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg to regulate the serum PTH and Ca concentrations to the normal levels.

Alternatively, another aspect of the present invention comprises a medicinal composition or a method for regulating the serum PTH concentration in a patient with secondary hyperparathyroidism on maintenance dialysis to the normal level, wherein the composition comprises Compound A, a pharmaceutically acceptable salt thereof or a solvate thereof, and the composition is intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg. The aspect further comprises a medicinal composition or a method for regulating the serum PTH and Ca concentrations in a patient with secondary hyperparathyroidism on maintenance dialysis to the normal level, wherein the composition comprises Compound A, a pharmaceutically acceptable salt thereof or a solvate thereof, and the composition is intravenously administered at the end of dialysis with a daily dose for adults selected from doses of 0.01 mg, 0.025 mg, 0.05 mg or more and from doses of 2.5 mg, 0.8 mg, 0.4 mg, 0.3 mg, 0.2 mg or less, preferably 0.025 mg-0.8 mg, more preferably 0.025-0.4 mg and still more preferably 0.05-0.2 mg.

The present invention also relates to a kit comprising Compound A, a pharmaceutically acceptable salt thereof or a solvate thereof, and a label and/or an attached instruction instructing a daily dose for intravenous administration in adults at the end of dialysis (for example, a dose of 0.025 mg-0.8 mg, more preferably 0.025-0.4 mg, and still more preferably 0.05-0.2 mg) for preventing or treating secondary hyperparathyroidism under maintenance dialysis.

The kit may further comprise a container for containing Compound A, a pharmaceutically acceptable salt thereof or a solvate thereof (for example, a vial, an ampoule) and/or a box (package) for packaging said container.

In the above-described kit, Compound A, a pharmaceutically acceptable salt thereof or a solvate thereof may be a medicinal composition containing Compound A, a pharmaceutically acceptable salt thereof or a solvate thereof and a pharmaceutically acceptable carrier (for example, sodium chloride, disodium hydrogen phosphate or a hydrate thereof, sodium dihydrogen phosphate or a hydrate thereof).

Effect of the Invention

The present invention can provide an agent for preventing or treating secondary hyperparathyroidism under maintenance dialysis with reduced side effects or without manifesting significant accumulating property, which allows easier dosage management by medical practitioners and which is a safer drug than conventional products, and thus is beneficial for both patients and medical practitioners.

MODE FOR CARRYING OUT THE INVENTION

Figure 1:
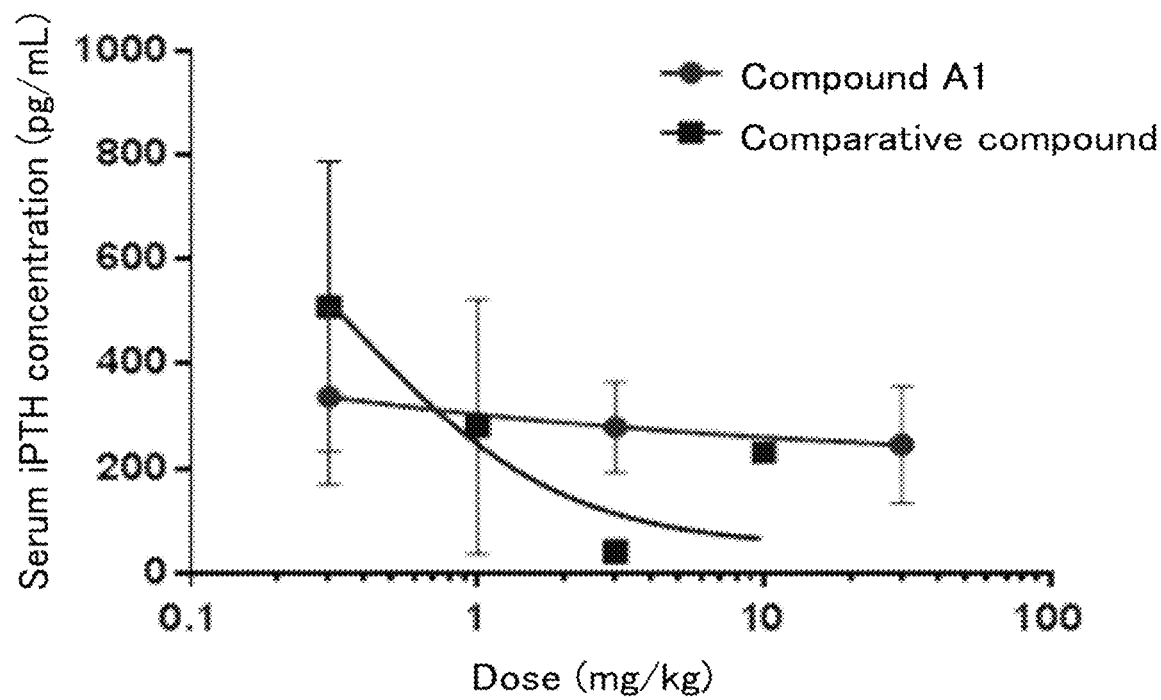
FIG. 1 A graph showing the relationship between the serum iPTH concentration and the given doses 48 hours after a single intravenous administration to the bilaterally nephrectomized rats in Example 2.

Hereinafter, the present invention will be described in more detail. The medicinal composition of the present invention can be used for a patient developing or having the risk of developing secondary hyperparathyroidism, specifically, a patient with a chronic kidney disease who is receiving dialysis on a continuous basis.

"Secondary hyperparathyroidism" refers to hyperparathyroidism that occurs from continuous presence of a factor stimulating the parathyroid glands, which is induced by abnormal bone mineral metabolism resulting from renal function disorders, and refers to a state where the serum PTH concentration prior to administration of the medicinal composition of the present invention is exceeding a certain range. A PTH concentration can be measured by various measurement methods, for example, as intact PTH (iPTH) which can be acquired by measuring only the full-length PTH, or as whole PTH which can be acquired by measuring only biologically active full-length PTH. Based on the reference values of dialysis patients which are defined for respective measurements, secondary hyperparathyroidism is diagnosed when the measured PTH values exceed a certain range. In general, secondary hyperparathyroidism is diagnosed in terms of iPTH value, specifically when iPTH exceeds 300 pg/ml, and in some cases when iPTH exceeds 240 pg/ml.

Here, in a case of hypoalbuminemia (albumin is 4 g/dl or less), a serum Ca concentration can be corrected by the following equation.

Corrected serum Ca level [mg/dl]=Measured serum Ca level [mg/dl]+4−Serum albumin level [g/dl]

"Prevention" of secondary hyperparathyroidism means to administer the medicinal composition of the present invention to a patient whose serum PTH concentration is within the reference range of dialysis patients prior to administration of the medicinal composition of the present invention but who is at risk of developing secondary hyperparathyroidism due to renal function disorders so that the measured serum PTH concentration does not exceed the upper limit of the reference value for dialysis patients.

"Treatment" of secondary hyperparathyroidism means to administer the medicinal composition of the present invention to a patient developing secondary hyperparathyroidism so as to lower the serum PTH concentration to be lower than the concentration prior to administration of the medicinal composition of the present invention, preferably to the reference value for dialysis patients. More preferably, it means to lower the serum PTH concentration but not to fall below the lower limit value of the reference value for dialysis patients and not to exceed the upper limit value of said reference value. Moreover, at the same time as lowering the serum PTH concentration to the reference value for dialysis patients, it may also mean to suppress the progression of parathyroid hyperplasia and mineral metabolism disorders (especially, Ca and P) which are symptoms relating to secondary hyperparathyroidism, preferably to improve the symptoms from how they were before administration of the medicinal composition of the present invention, or to keep the parameters relative to the mineral metabolism disorder within the reference values for dialysis patients.

"A daily dose" of Compound A "for adults selected from doses of 0.01 mg, 0.025 mg, 0.05 mg or more and from doses of 2.5 mg, 0.8 mg, 0.4 mg, 0.3 mg, 0.2 mg or less" refers to any dose in a range of 0.01 mg-2.5 mg, 0.01 mg-0.8 mg, 0.01 mg-0.4 mg, 0.01 mg-0.3 mg, 0.01 mg-0.2 mg, 0.025 mg-2.5 mg, 0.025 mg-0.8 mg, 0.025 mg-0.4 mg, 0.025 mg-0.3 mg, 0.025 mg-0.2 mg, 0.05 mg-2.5 mg, 0.05 mg-0.8 mg, 0.05 mg-0.4 mg, 0.05 mg-0.3 mg or 0.05 mg-0.2 mg. If Compound A is a solvate, the dose refers to an amount of Compound A in terms of a nonsolvate. If Compound A is a solvate of a salt, the dose refers to an amount of free Compound A in terms of a nonsolvate. If the patient is Japanese, the dose is preferably 0.025 mg-0.8 mg, more preferably 0.025-0.4 mg, and still more preferably 0.05-0.2 mg. The preferred given dose may vary among races. For example, the Caucasoid, Australoid and Negroid generally require a higher given dose than that preferred for the Mongoloid such as Japanese.

Since the medicinal composition of the present invention is administered at the time of dialysis (upon dialysis), if the general dialysis schedule consists of three sessions a week, the medicinal composition of the present invention is administered upon each dialysis session. In this case, assuming that the beginning of a week is Day 1, dialysis is conducted, for example, on Days 1, 3, and 5, upon which the medicinal composition of the present invention is administered, and the same schedule is repeated from next week and on. If the dialysis schedule consists of 4 sessions a week, or if more than 4 sessions are temporarily conducted due to the patient condition or the like, the medicinal composition of the present invention is administered following the same schedule of 4 or more dialysis sessions a week. Preferably, the medicinal composition of the present invention is administered at the end of each dialysis session in the dialysis schedule of 3-5 sessions a week.

The phrase "the end of dialysis" means immediately before the end of dialysis, specifically, when the blood is returned immediately before the end of dialysis.

The phrase "intravenously administered" means to directly administer the drug into the vein, but, for dialysis patients, it is preferable to administer the drug from the venous side of the dialysis circuit.

More preferably, the drug is infused into the venous side of the dialysis circuit upon returning the blood at the end of dialysis.

The term "side effects" refers to side effects that have been a problem of an existing drug having the same indications, specifically, digestive symptoms such as nausea and vomiting, hypersensitivity reaction, dysgeusia, hypocalcemia, exacerbation of heart failure caused by hypocalcemia, QT prolongation, numbness, a muscle spasm, sick feeling, arrhythmia, hypotension and a spasm.

The term "reduced side effects" means that occurrence of side effects caused by an existing drug having the same indications is lower than said existing drug when administration is conducted with a specific dosage and administration according to the present invention. Specifically, it means that occurrence of said side effects is 20% or less, 15% or less, 10% or less, 5% or less, and preferably 1% or less in a patient given with the medicinal composition of the present invention.

The phrase "without manifesting significant accumulating property" means that even if the medicinal composition of the present invention is continuously administered (for 1 month or more) with a defined dosage and administration, the concentration of Compound A in the blood is not significantly increased in proportion to the period of administration.

The phrase "used for long-term administration" means that it is a medicinal composition with fewer cases of medication discontinuation, which is more adaptable to long-term administration as compared to an existing drug having the same indications (cinacalcet, etelcalcetide). Specifically, it refers to continuous administration of 1 year or longer.

The phrase "regulate to the normal level" means to regulate the serum PTH or Ca concentration to a level that is judged to be clinically unproblematic by the physician, preferably, to be within the range of the reference values for dialysis patients defined for the respective inspection values. More preferably, it means that regulation to the above-mentioned level is conducted by administration within a defined dosage and administration range without any break from medication during the period of administration.

In general, the serum iPTH concentration is in a range of 60 pg/ml to 300 pg/ml, preferably in a range of 150 pg/ml to 300 pg/ml or 60 pg/ml to 240 pg/ml.

The reference serum Ca concentration of the dialysis patients (corrected serum Ca concentration in case of hypoalbuminemia) is generally in a range of 8.4 mg/dl to 10.0 mg/dl.

Note that the normal level also includes cases where there is no need of discontinuing the administration even though the concentration may temporarily deviate from the above-mentioned reference range.

The present invention comprises a medicinal composition that contains Compound A, a pharmaceutically acceptable salt thereof or a solvate thereof as an active ingredient and a pharmaceutically acceptable carrier such as a pharmaceutically acceptable nontoxic carrier, and also comprises a medicine consisting only of Compound A, a pharmaceutically acceptable salt thereof or a solvate thereof.

Compound A used for the present invention also comprises Compound A in a salt form. If Compound A, an active ingredient of the present invention, is in a salt form, the salt is a pharmaceutically acceptable salt or an edible salt. Examples of salts of an acidic group such as the carboxyl group in the formula include an ammonium salt, a salt with a metal such as sodium, potassium, calcium, magnesium, aluminum or zinc, a salt with an organic amine such as triethylamine, ethanolamine, morpholine, pyrrolidine, piperidine, piperazine or dicyclohexylamine, and a salt with a basic amino acid such as arginine or lysine. Examples of salts of a basic group include a salt with an inorganic acid such as hydrochloric acid, sulfuric acid, phosphoric acid, nitric acid or hydrobromic acid, a salt with an organic carboxylic acid such as acetic acid, trifluoroacetic acid, citric acid, benzoic acid, maleic acid, fumaric acid, tartaric acid, succinic acid, tannic acid, butyric acid, hibenzic acid, pamoic acid, enanthic acid, decanoic acid, teoclic acid, salicylic acid, lactic acid, oxalic acid, mandelic acid or malic acid, and a salt with an organic sulfonic acid such as methanesulfonic acid, benzenesulfonic acid or p-toluenesulfonic acid. These salts can be produced by making said compound into contact with an acid or a base that can be used for producing a pharmaceutical product.

Preferably, it is sodium salt of Compound A.

According to the present invention, Compound A or a salt thereof may be an anhydride, and may form a solvate such as a hydrate or an alcohol adduct. As used herein, "solvation" refers to a phenomenon where solute molecules or ions strongly attract the surrounding solvent molecules and form a single molecular cluster in a solution. For example, it is called hydration if the solvent is water. The solvate may be either a hydrate or a nonhydrate. A nonhydrate may use an alcohol (for example, methanol, ethanol, n-propanol), dimethylformamide or the like.

Preferably, it is a hydrate of sodium salt of Compound A.

If Compound A is obtained in a free form, it may be converted into a form of a salt, a hydrate thereof or a solvate thereof that may result from said compound, according to a conventional procedure.

Moreover, if Compound A is obtained as a salt, a hydrate or a solvate of said compound, it may be converted into a free form of Compound A, according to a conventional procedure.

Compound A is intravenously administered as a medicinal composition containing Compound A as an active ingredient. The method for applying such a medicinal composition is not particularly limited and the composition may be administered in a form of a commonly employed medicine formulation by mixing the active ingredient with a pharmaceutically acceptable nontoxic liquid carrier that is suitable for administration such as injection.

Examples of such a formulation include forms of liquid agents such as a solution, a suspension and an emulsion, and forms such as a lyophilized agent. These formulations can be prepared by a pharmaceutically common process.

Examples of the pharmaceutically acceptable nontoxic carrier include water and physiological saline. In addition, if necessary, a common additive such as a pH control agent, a stabilizer, an emulsifier or a tonicity agent may also suitably be added.

The medicinal composition of the present invention can be formulated by a conventional procedure. In accordance with the pharmaceutical need, various pharmacologically acceptable substances for formulation may be added (as adjuvants or the like). The substance for formulation may appropriately be selected in accordance with the dosage form of the formulation. For example, if the formulation is a solution, examples of the substance for formulation include sterilized water and a monohydric or polyhydric alcohol such as glycerol.

The medicinal composition of the present invention may include an insert instructing the use thereof inside the package. An example of such an insert includes so-called instructions explaining the usage, efficacy, administration method and the like.

In accordance with symptoms of the patient, the medicinal composition of the present invention may be used in combination with a calcium agent or a vitamin D formulation. The dosage and administration of the calcium agent or the vitamin D formulation used in combination can appropriately be determined according to the blood Ca concentration.

EXAMPLES

Hereinafter, the present invention will be described specifically by means of examples, although the present invention should not be interpreted to be limited to these examples.

Example 1: Synthesis of sodium 3-{[(2S)-2-amino-2-carboxyethyl]carbamoylamino}-5-chloro-4-methylbenzenesulfonate (Compound A1)

(Step 1)
Synthesis of 3-({[(2S)-2-amino-3-methoxy-3-oxopropyl]carbamoyl}amino)-5-chloro-4-methylbenzene-1-sulfonic acid To 5 g (22.56 mmol) of 3-amino-5-chloro-4-methylbenzenesulfonic acid (ACTS), 37.5 mL (7.5 L/kg vs ACTS) of acetonitrile, 3.81 mL (47.38 mmol, 2.1 eq.) of pyridine were added and stirred at 25° C. 2.99 mL (23.68 mmol, 1.05 eq.) of ClCO$_2$Ph was dropped into the resultant, which was stirred for 30 minutes and thereafter the end of carbamate reaction was confirmed by HPLC. 5.92 g (23.23 mmol, 1.03 eq.) of 3-amino-N-(tert-butoxycarbonyl)-L-alanine methyl ester hydrochloride was added and 9.75 mL (69.93 mmol, 3.1 eq.) of triethylamine was dropped into the resultant, which was stirred at 25° C. for 3 hours. 0.4 g (1.58 mmol, 0.07 eq.) of 3-amino-N-(tert-butoxycarbonyl)-L-alanine methyl ester hydrochloride and 0.22 mL (1.58 mmol, 0.07 eq.) of triethylamine were further added, and the end of urea-forming reaction was confirmed by HPLC. 7.32 mL (112.8 mmol, 5.0 eq.) of methanesulfonic acid was added, and the resultant was heated to 50° C. and stirred for 4 hours.

After confirming the end of deprotection by HPLC, the resultant was cooled to 25° C. and added with 37.5 mL (7.5 L/kg) of acetonitrile and 7.5 mL (1.5 L/kg) of water to allow deposition of a solid. The resultant was cooled to 5° C. and matured for 16 hours. The deposited solid was filtrated under reduced pressure, washed with 20 mL (4.0 L/kg) of water/acetonitrile (½), and then dried under reduced pressure at 40° C. for 5 hours to give 7.72 g of the compound of interest as a white solid (net 7.20 g, 87.3%).

$^1$H-NMR (400 MHz, DMSO-d6): δ8.39 (bs, 3H), 8.16 (d, 1H, J=1.2 Hz), 7.90 (d, 1H, J=1.6 Hz), 7.28 (d, 1H, J=1.6 Hz), 6.78 (t, 1H, J=5.6 Hz), 4.20-4.10 (m, 1H), 3.77 (s, 3H), 3.70-3.60 (m, 1H), 3.55-3.45 (m, 1H), 2.21 (s, 3H)

HRMS (FAB$^-$): calcd for m/z 364.0369 (M-H), found m/z 364.0395 (M-H).

(Step 2)

(2) Synthesis of sodium 3-{[(2S)-2-amino-2-carboxyethyl]carbamoylamino}-5-chloro-4-methylbenzenesulfonate To 10.64 g (net 10.0 g, 27.34 mmol) of the compound obtained in Step 1, 18 mL (1.8 L/kg vs compound of Step 1) of water was added and the resultant was stirred at 8° C. 3.42 mL (57.41 mmol, 2.1 eq.) of a 48% aqueous sodium hydroxide solution was dropped into the resultant, which was washed with 1.0 mL (1.0 L/kg) of water and then stirred at 8° C. for 15 minutes. After confirming the end of hydrolysis by HPLC, the resultant was heated to 25° C., to which about 3.55 mL of 48% HBr aq. was added to control pH to 5.8. 65 mL (6.5 L/kg) of isopropyl alcohol was dropped into the resultant. After confirming deposition of the compound of interest, the resultant was matured for an hour. 81 mL (8.1 L/kg) of isopropyl alcohol was dropped into the resultant and matured at 8° C. overnight. The deposited solid was filtrated under reduced pressure, washed with 20 mL (2.0 L/kg) of isopropyl alcohol, and dried under reduced pressure at 40° C. for 4 hours to give 10.7 g of the compound of interest as a white solid (net 9.46 g, 92.6%).

$^1$H-NMR (400 MHz, DMSO-d6): δ8.76 (s, 1H), 7.91 (d, 1H, J=1.6 Hz), 8.00-7.50 (bs, 2H), 7.24 (d, 1H, J=1.6 Hz), 7.20 (t, 1H, J=5.6 Hz), 3.58-3.54 (m, 1H), 3.47-3.43 (m, 1H), 3.42-3.37 (m, 1H), 2.23 (s, 3H)

Example 2: Effect of Compound A1 on Serum Ca Concentration and Serum iPTH Concentration in Bilaterally Nephrectomized Rats After quarantine and acclimatization periods of 6 days, fifty-one 7-week-old rats (Crl: CD (SD), male) were fed a 100% sucrose diet ad libitum from four days before the surgery. On the day of the surgery, skin incisions were made on the back at the sites of the right and left kidneys under isoflurane anesthesia and the renal capsules were removed to ligate the renal arteries and veins and the ureters using threads before removing the right and left kidneys. A penicillin solution was given upon suturing, and 5 mL of physiological saline was intraperitoneally administered before returning the rats into the breeding cages.

On the day of administering the test substance, i.e., a day after the bilaterally nephrectomy, approximately 100 μL of blood was collected from the tail vein without anesthesia using a capillary tube, which was centrifuged in a high speed refrigerated microcentrifuge (10000 rpm, 5 min, 4° C.) to separate the serum. Thereafter, the serum Ca concentration was measured with a dri-chem analyzer (model number: FUJI DRI-CHEM 7000, manufacturer: FUJIFILM Medical Co. Ltd.) to select individuals with a serum Ca concentration of 8.0 mg/dL or more and less than 14.0 mg/dL.

On a day after the bilaterally nephrectomy, the given doses were calculated based on the weight of the selected animals on that day. Group 1 was given a medium (physiological saline), Groups 2, 3 and 4 were given the Compound A1 solution (0.3, 3 and 30 mg/mL, respectively), and Groups 5, 6, 7 and 8 (5 rats per group) were given the comparative compound (0.3, 1, 3 and 10 mg/mL, respectively), each given a single dose of 1 ml/kg from the tail vein. Prior to the administration (0 hour), and 24 and 48 hours after the administration, approximately 300 μL of blood was collected without anesthesia from the tail vein using capillary tubes for obtaining the serum. The blood for obtaining the serum was left to stand at room temperature, and centrifuged in a high speed refrigerated microcentrifuge (10000 rpm, 5 min, 4° C.) within a period of 30 minutes to 2 hours after the blood collection to collect the serum.

Thereafter, the serum Ca was analyzed with COBAS analyzer (Model number: COBAS INTEGRA 400 plus, manufacturer: Roche Diagnostics K.K.), and the remaining serum was stored in an ultra-low freezer (temperature set to −80±15° C.) until the day of iPTH measurement. On the day of iPTH measurement, the serum was melted at room temperature for measurement.

(Compound A1 Solutions)

A 30 mg/ml Compound A1 solution (338 mg of Compound A1 dissolved in 10 ml of physiological saline) was diluted with physiological saline to prepare 0.3 mg/ml and 1 mg/ml Compound A1 solutions.

(Comparative Compound Solutions)

149 mg of etelcalcetide (Ac-c(C) arrrar-NH$_2$) TFA salt (WO 2011014707) was prepared to have pH of 6-8 with 7 ml of physiological saline and a 0.5N aqueous NaOH solution, to which physiological saline was further added to make 10 ml. The prepared 10 mg/ml comparative compound solution was diluted with physiological saline to give 0.3 mg/ml and 1 mg/ml comparative compound solutions.

(Results)

(1) Serum iPTH Concentration in Bilaterally Nephrectomized Rats

The mean±standard error of the serum iPTH concentrations of all individuals prior to the administration (0 hour) was 231±16 pg/ml. Administrations of Compound A1 at 0.3, 3 and 30 mg/kg decreased the serum iPTH concentrations, where the means were 140, 138 and 118 mg/dL 24 hours after the administration, respectively, and 338, 280 and 245 mg/dL 48 hours after the administration, respectively. Here, the plasma Compound A1 concentration 48 hours after a single intravenous dose of Compound A1 at 30 mg/kg in the bilaterally nephrectomized rats was estimated to be 18.8 μg/ml, maintaining sufficiently higher concentration than the 50% effective concentration, i.e., EC$_{50}$ value, of 75 ng/ml for decreasing the serum iPTH concentration.

Meanwhile, administrations of the comparative compound at 0.3, 1, 3 and 10 mg/kg also decreased the serum iPTH concentration, where the mean serum iPTH concentrations were 122, 52, 22 and 104 mg/dL 24 hours after the administration, respectively, and 510, 280, 41 and 230 (n=1) mg/dL 48 hours after the administration, respectively. Here, the concentration of the comparative compound in the plasma 48 hours after a single intravenous dose of the comparative compound at 3 mg/kg in the bilaterally nephrectomized rats was estimated to be 0.13 μg/ml, maintaining sufficiently higher concentration than the 50% effective concentration, i.e., EC$_{50}$ value, of 40 ng/ml for decreasing the serum iPTH concentration. Logistic curve fitting was conducted to establish the response relationship between the serum iPTH concentration 48 hours after the administration and the given dose. As a result, the lower limit values of the serum iPTH concentrations by administrations of Compound A1 and the comparative compound were simulated to be 203.0 pg/ml and 48.18 pg/ml, respectively (FIG. 1).

(2) Serum Ca Concentration in Bilaterally Nephrectomized Rats

The mean±standard error of the serum Ca concentration of all individuals prior to the administration (0 hour) was 11.25±0.28 mg/dL.

Administrations of Compound A1 at 0.3, 3 and 30 mg/kg decreased the serum Ca concentrations, where the means were 9.07, 7.97 and 7.99 mg/dL 24 hours after the administration, respectively, and 10.24, 8.55 and 8.14 mg/dL 48 hours after the administration, respectively.

Meanwhile, administrations of the comparative compound at 0.3, 1, 3 and 10 mg/kg also decreased the serum Ca concentration, where the mean serum Ca concentrations were 8.33, 6.42, 6.82 and 6.95 mg/dL 24 hours after the administration, respectively, and 10.44, 7.33, 5.85 and 6.65 (n=1) mg/dL 48 hours after the administration, respectively.

Figure 2:
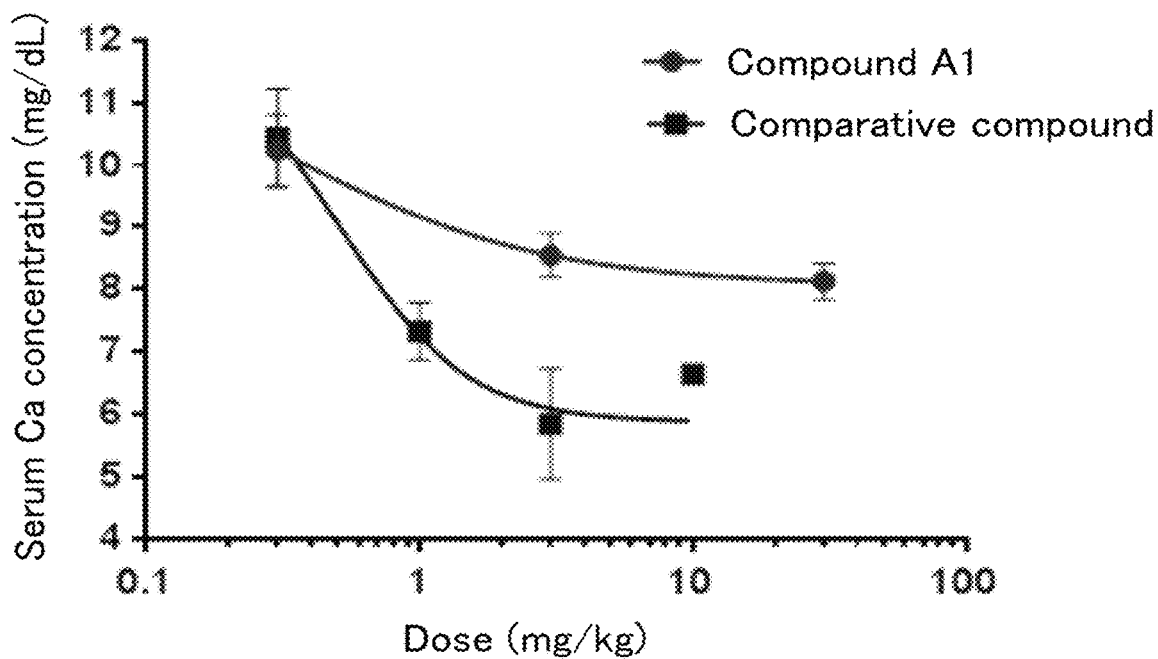
FIG. 2 A graph showing the relationship between the serum Ca concentration and the given doses 48 hours after a single intravenous administration to the bilaterally nephrectomized rats in Example 2.

Logistic curve fitting was conducted to establish the response relationship between the serum Ca concentration 48 hours after the administration and the given dose. As a result, the lower limit values of the serum Ca concentrations by administrations of Compound A1 and the comparative compound were simulated to be 8.072 mg/dL and 5.880 mg/dL, respectively (FIG. 2).

Figure 3:
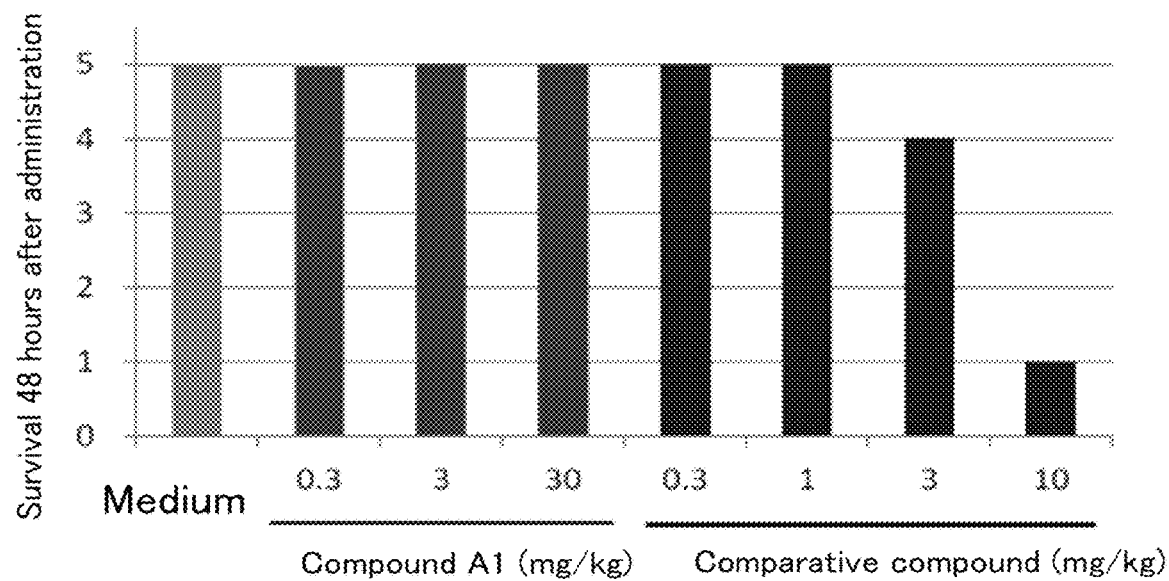
FIG. 3 A chart comparing the survival 48 hours after a single intravenous administration to the bilaterally nephrectomized rats in Example 2.

(3) Survival of Bilaterally Nephrectomized Rats After Single Doses of Compound A1 and Comparative Compound The number of rats in each group was five prior to the administration. While all five rats survived 48 hours after the administration in the medium-administered group and the Compound A1-administered groups, four survived in the 3 mg/kg group and one survived in the 10 mg/kg group among the comparative compound-administered groups (FIG. 3).

Compound A1 is a CaSR activator used for intravenous administration. Non-clinical studies show that renal excretion is the main route of excretion, and when the compound is intravenously administered to a normal rat, the compound is rapidly eliminated from the plasma. In renal failure rat models, serum iPTH and Ca concentrations sufficiently decreased during the 48 hours after the administration but the decreases were gradual with respect to the increase in the dose.

On the other hand, already launched etelcalcetide having the same action mechanism decreased the serum iPTH and Ca concentrations in a dose-dependent manner, but the number of dead rats increased in a dose-dependent manner.

These results show that Compound A1, as compared to etelcalcetide, had advantageous effect of not decreasing the serum iPTH and Ca concentrations to an extent affecting maintenance of life, and that it was useful for controlling the serum iPTH and Ca concentrations in nephropathy patients.

Example 3: Studies of Emetogenicity of Compound A1 in Dogs

A crossover trial was conducted with male beagles (Nosan Beagle, 14-87-month-old, weight: 10.2 kg-15.8 kg). The Compound A1 solutions used in Example 2 were given at 0.3, 1 and 10 mg/kg by bolus administration (0.5 mL/kg, 1 mL/sec) to 3-6 dogs per dose to confirm the manifestation of vomiting immediately after the administration. Administration was conducted once or twice a week with a 2-day interval. Administration was conducted prior to feeding.

Symptoms prior to, immediately after, and 15 and 30 minutes after the administration were observed.

(Results)
The results are shown in Table 1.

TABLE 1

| | Status of vomiting | | |
|---|---|---|---|
| | Route of administration | Dose (mg/kg) | Number of vomiting cases/ Number of administration |
| Compound A1 | Intravenous | 0.3 | 0/3 |
| | | 1 | 0/3 |
| | | 10 | 1/6 |

For administration at 1 mg/kg with no vomiting case in the dogs, $C_0$ was 18.8 μM. Assuming that an effective dose in human was 0.1 mg/man in view of Example 5 below, $C_0$ was 0.0436 μM based on the analysis results acquired by simultaneously fitting all doses.

From the above results, Compound A1 was found to have a 430 times or more higher therapeutic margin in human than in dogs with respect to vomiting.

Cinacalcet is known to frequently manifest digestive symptoms such as nausea and vomiting, which are factors that inhibit continuous administration. On the other hand, since the dose of Compound A1 of the present invention given to human greatly differs from the dose that manifests vomiting in dogs, it appears to be a medicinal composition that has few side effect such as vomiting in human, that is safe and that is adaptable to long-term administration.

Example 4: Histamine Release Test Using Rat Peritoneal Mast Cells

SD male rats (10-week-old) were used to isolate rat peritoneal mast cells according to the method of Kimura et al. (Kimura T., Eur J Pharmacol. 2000 Nov. 3; 407(3): 327-32). Compound A1 was added to these mast cells to determine the amount of released histamine according to the method of Liu J et al. (Liu J J Chromatogr B Analyt Technol Biomed Life Sci. 2014 Nov. 15; 971: 35-42) to compare the effects of Compound A1, the comparative compound, and Compound 48/80 as positive control on histamine release. Specifically, the test substance was added to the peritoneal cell suspension obtained from SD rats (cell concentration of $0.4 \times 10^5$ cells/ml), and determined the histamine concentration in the cell supernatant after incubated at 37° C. for 30 minutes. Here, etelcalcetide was used as the comparative compound; Compound A1 and the comparative compound were each prepared into five groups of 0.1 μM-1000 μM in the same manner as Example 2; and Compound 48/80 (manufactured by Sigma) was tested at concentrations of 0.1 mg/ml and 10.0 mg/ml.

The inhibition ratio was calculated by the following equation.

Inhibition ratio (%)=(Histamine concentration of individual group (μM)−Histamine concentration of negative control group (μM))×100/(Total histamine concentration (μM)−Histamine concentration of negative control group (μM))

Figure 4:
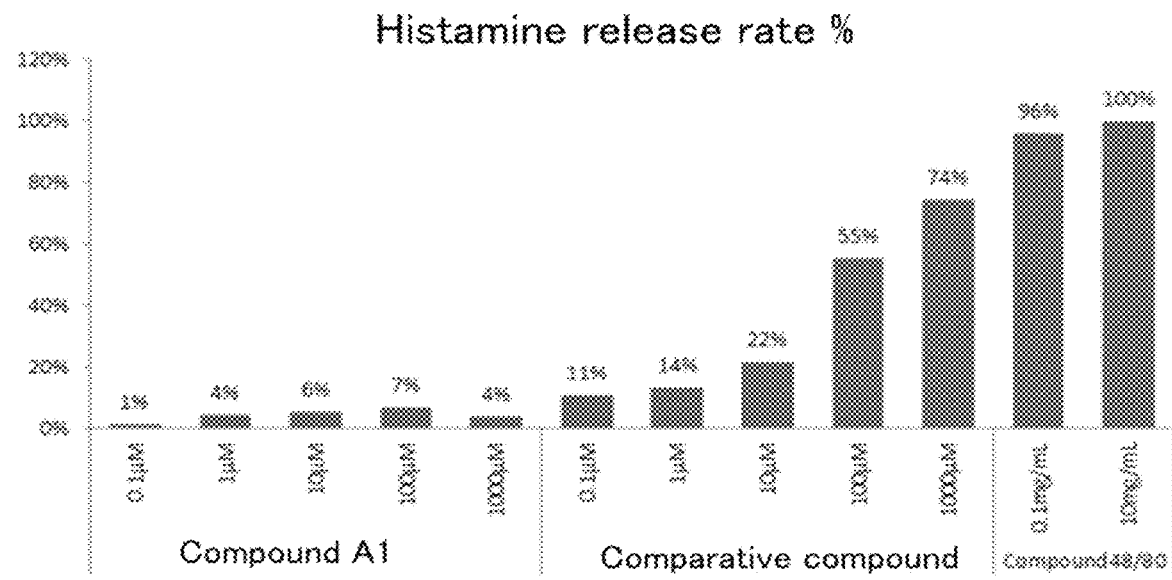
FIG. 4 A chart showing histamine release rate from peritoneal mast cells upon administering the respective compounds in Example 4.

(Results)
As can be appreciated from FIG. 4, Compound A1 was shown to induce almost no histamine release. Meanwhile, the comparative compound increased the released histamine level in a dose-dependent manner.

Etelcalcetide is known to have the risk of developing hypersensitivity reaction, and thus requires great caution upon administration. On the other hand, since Compound A1 of the present invention hardly causes histamine release which is a major cause of hypersensitivity reaction, it has a low probability of developing hypersensitivity reaction and thus was confirmed to be a medicinal composition with reduced side effects.

Example 5: Phase I Clinical Trial and Determination of Clinically Effective Amount (1) Phase I Clinical Trial (P1)

Thirty-two healthy Japanese male adults were given a single intravenous dose of the test drug (Compound A1) at 0.01 mg, 0.1 mg, 1.0 mg or 2.5 mg in a fasted state to study the pharmacokinetics, pharmacodynamics and safety by a double-blind test using a placebo as a control. Here, the trial drug was administered by diluting a required dose taken from the Compound A1 vial formulation prepared as follows with sterilized water for injection, and filling a syringe with the resultant in accordance with the dose to be administered.

(Compound A1 Vial Formulation)

A vial formulation encapsulating 100 mg of Compound A1 in terms of a dehydrate, and sodium chloride, disodium hydrogen phosphate dodecahydrate and sodium dihydrogen phosphate dihydrate as additives in 10 ml of sterilized water for injection (Placebo)

A vial formulation encapsulating 10 ml of sterilized water for injection without Compound A1

(Results)

In the phase I trial that targeted healthy male adults and that used a placebo as a control, single intravenous doses of 0.01 mg, 0.1 mg, 1.0 mg and 2.5 mg Compound A1 were present as generally unchanged substances in the plasma and rapidly eliminated.

Furthermore, since they were excreted into the urine mostly as unchanged substances with respect to the given dose, renal excretion was found to be the main elimination pathway of the unchanged substance. In the pharmacodynamic evaluations, the serum iPTH concentration was confirmed to have decreased in the 0.01 mg and higher dose groups as compared to that before the administration, where the duration of decreased serum iPTH concentration extended with the increase in the given dose. As to safety, non-severe and mild side effects such as vomiting were observed in the 1.0 mg and higher dose groups, but no other problematic event was observed.

(2) Determination of Clinically Effective Amount

A PK/PD analysis was conducted to estimate the clinically effective dose based on the results from P1. The dose of 2.5 mg seemed to be excessive and thus was eliminated from the analysis. PK (mean plasma concentration) and PD (mean iPTH level normalized by the levels of the placebo group and the 0-hour level) data of the doses of 0.01 mg, 0.1 mg and 1 mg were used. An indirect response model incorporating rebound was used for the PK/PD analysis.

Figure 5:
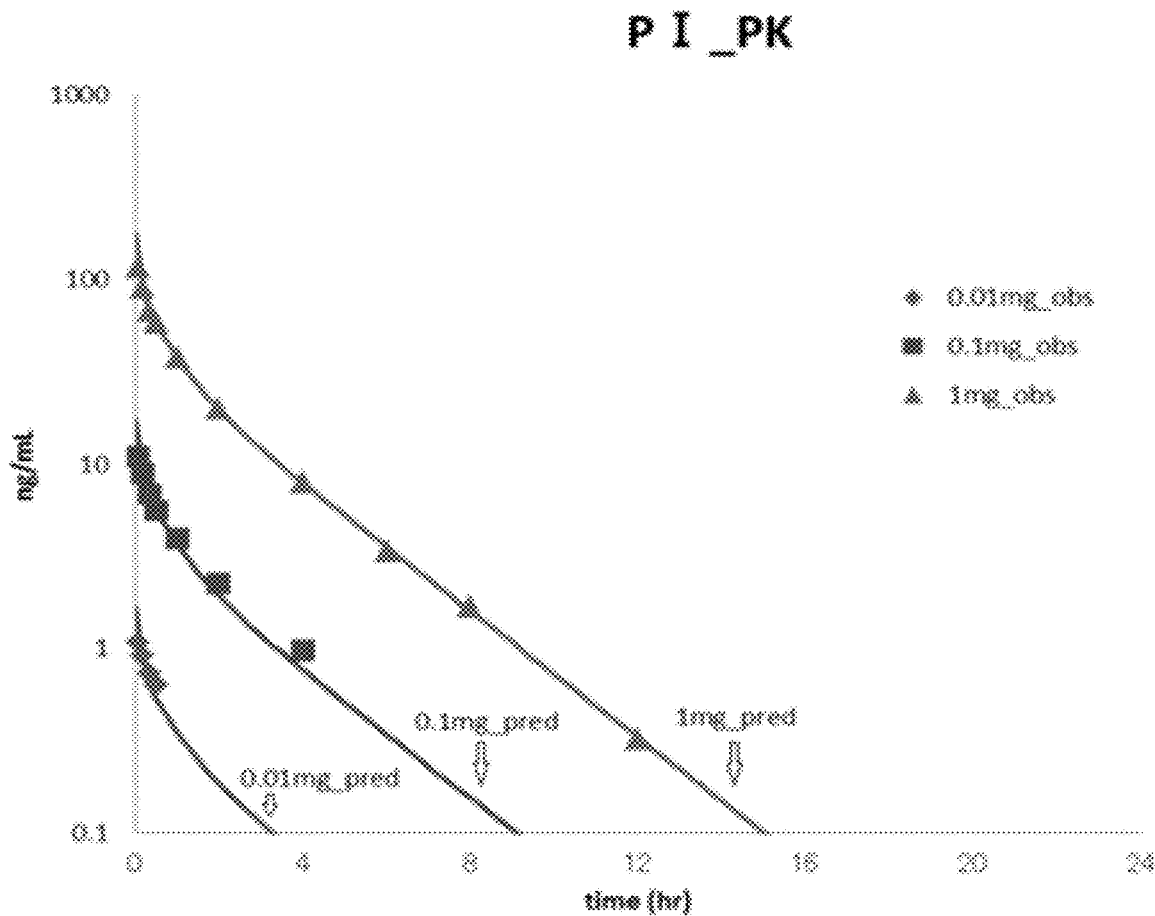
FIG. 5 A graph obtained by simultaneously fitting changes in the plasma concentrations for the three given doses in P1 using a three-compartment model.

Based on the results of PK of the three given doses (0.01 mg, 0.1 mg and 1 mg) in P1, the three given doses were simultaneously analyzed using a three-compartment model to calculate the PK parameters (FIG. 5 and Table 2).

TABLE 2

PK parameters obtained by simultaneously fitting changes in the plasma concentrations for the three given doses in P1 using a three-compartment model

| | PK parameter (± standard error) |
|---|---|
| Vd (mL/kg) | 90.9 ± 11.4 |
| Ke (hr-1) | 1.28 ± 0.15 |
| K12 (hr-1) | 0.658 ± 0.136 |
| K21 (hr-1) | 0.819 ± 0.049 |
| K13 (hr-1) | 4.42 ± 1.80 |
| K31 (hr-1) | 6.89 ± 1.33 |

Figure 6:
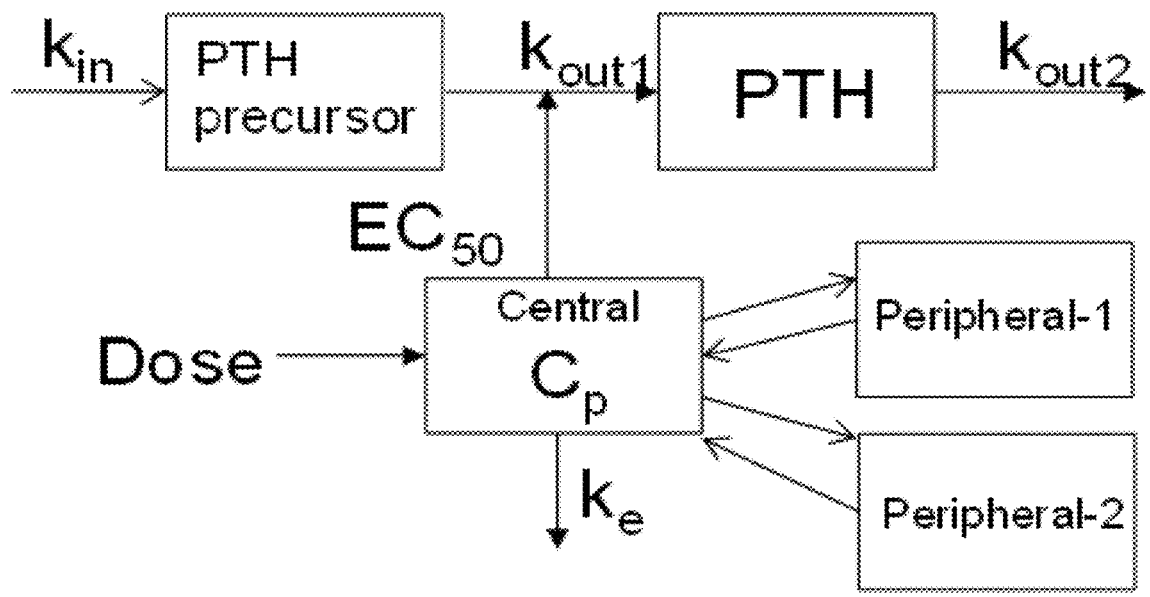
FIG. 6 A schematic view showing an indirect response model incorporating rebound.
Figure 7:
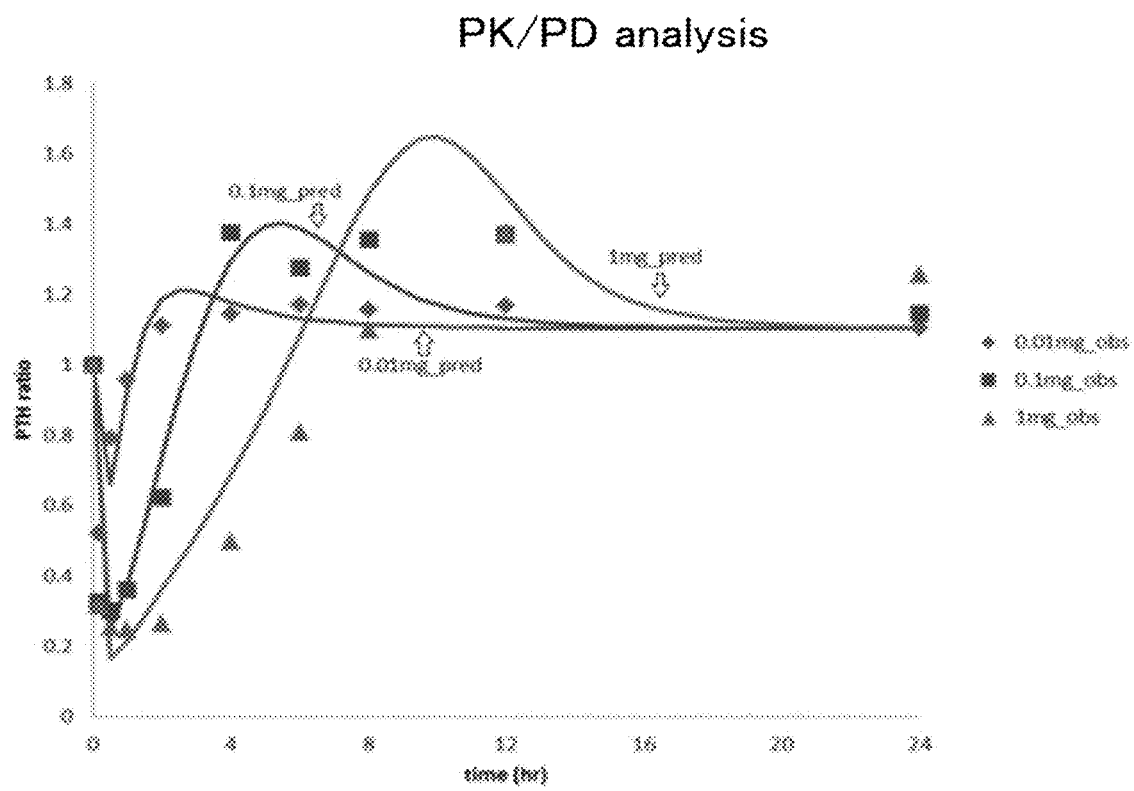
FIG. 7 A graph of the PK/PD analysis based on P1 using the indirect response model incorporating rebound.

Using the calculated PK parameters as an input function, PK/PD analysis was performed using an indirect response model incorporating rebound (FIG. 6) to calculate the $EC_{50}$ value in healthy adults (FIG. 7 and Table 3).

TABLE 3

PD parameters by PK/PD analysis of P1 using indirect response model incorporating rebound

| | PD parameter (± standard error) |
|---|---|
| $EC_{50}$ (ng/mL) | 0.421 ± 0.167 |
| Emax (ratio) | 0.920 ± 0.027 |

$EC_{50}$ value in patient with renal failure was estimated based on the calculated $EC_{50}$ value in healthy adults and the results from the same analysis in normal rats and adenine-treated rat models (pathological rat models). First, $EC_{50}$ values were calculated in the same manner in rats, which were <22.9 ng/mL in normal rats and 74.8 ng/mL in adenine-treated rat models. Since the difference in the $EC_{50}$ value between rats in normal state and pathological state is presumed to be caused by the changes in PK that are considered to greatly vary between normal state and pathological state, similar tendency is expected in human as well. Accordingly, the scaling factor of $EC_{50}$ values of the heathy individuals and the patients with renal failure was set to ">3.3". This scaling factor was applied to human, whereby $EC_{50}$ value was estimated to be >1.4 ng/ml in the patients with renal failure.

Figure 8:
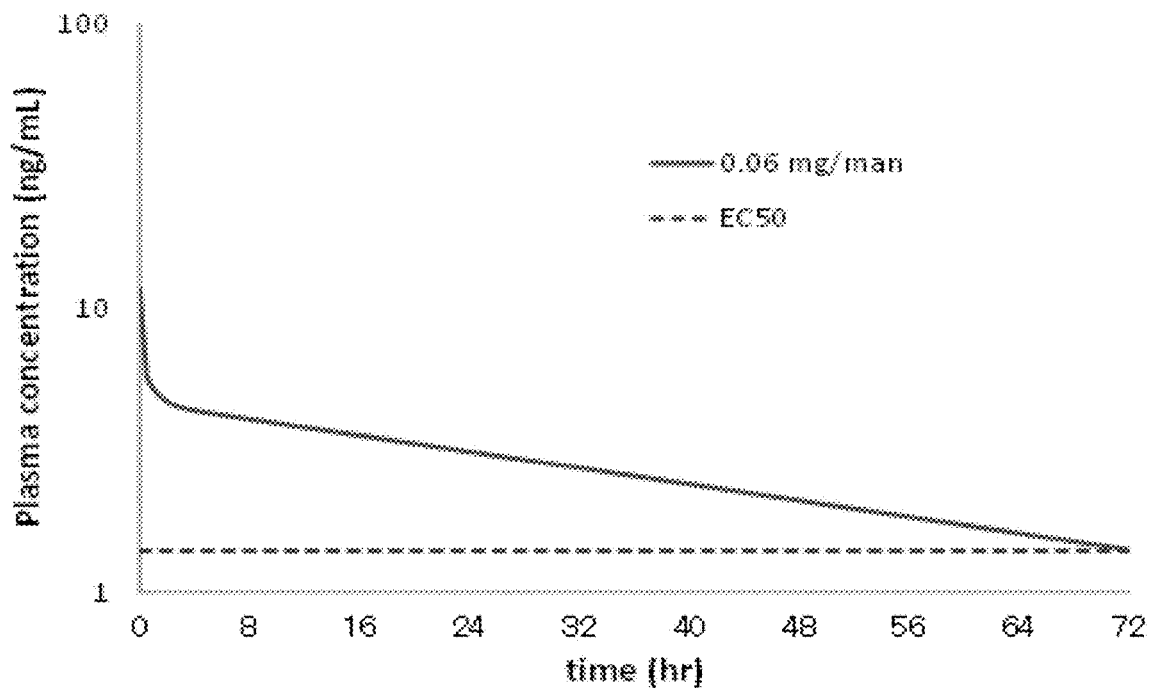
FIG. 8 A graph showing the expected PK and the deduced $EC_{50}$ value (>1.4 ng/ml) in patients on dialysis.

The result from PK fitting, and the contribution rate of renal elimination of the drug (3.2%) calculated using PK-sim (registered trademark) were used to simulate PK prediction in the patients with renal failure. This simulation for PK prediction and the previously estimated $EC_{50}$ value in the patients with renal failure (>1.4 ng/mL) were used to estimate a given dose that allows the plasma concentration of the drug to maintain the $EC_{50}$ value for 72 hours in the patients with renal failure, which was assumed to be the estimated clinically effective dose. As a result, administration of a dose of 0.06 mg/man was estimated to maintain a concentration higher than 1.4 ng/ml for 72 hours (FIG. 8). The clinically effective dose was estimated to be 0.1 mg/man considering that its $EC_{50}$ value exceeds 1.4 ng/ml.

Example 6: Phase I/II Clinical Trials

Targeting SHPT patients on maintenance hemodialysis, pharmacokinetics, pharmacodynamics and safety upon single or repeated intravenous administration of Compound A1 were examined by conducting a double-blind test using a placebo as a control.

Single administration: Based on the clinically effective dose calculated in Example 5, the doses were given at 0.025 mg, 0.05 mg, 0.1 mg, 0.2 mg, 0.4 mg, 0.6 mg and 0.8 mg (7 steps). On the day of trial drug administration, the trial drug was intravenously administered as slow as possible within 60 seconds 2 to 4 hours following the end of dialysis. Here, the trial drug was administered by diluting a required dose taken from the Compound A1 vial formulation prepared as follows with sterilized water for injection, and filling a syringe with the resultant in accordance with the dose to be administered.

Repeated administration: Based on the clinically effective dose calculated in Example 5, the doses were given in 3 steps, namely, 0.05 mg, 0.1 mg and 0.2 mg. The trial drug was (intravenously) infused from the venous side of the dialysis circuit before the end of dialysis three times a week for 22 days (total of 9 times) starting from the first day of administration of the trial drug. Here, the trial drug was administered by diluting a required dose taken from the Compound A1 vial formulation prepared as follows with sterilized water for injection, and filling a syringe with the resultant in accordance with the dose to be administered.

Each item was evaluated according to the predetermined evaluation schedule.

(Compound A1 Vial Formulation)

A vial formulation encapsulating 1 mg of Compound A1 in terms of a dehydrate, and sodium chloride, disodium hydrogen phosphate dodecahydrate and sodium dihydrogen phosphate dihydrate as additives in 10 ml of sterilized water for injection (Placebo)

A vial formulation encapsulating 10 ml of sterilized water for injection without Compound A1

(Results)

(1) Single administration: 44 cases (Compound A1-administered groups: 29 cases, placebo group: 15 cases)

Pharmacokinetic evaluation: Cmax and AUC of Compound A1 in plasma increased with the increase in the given dose. $t_{1/2}$ was 65.0-122 hours. When hemodialysis was performed 66 hours after the administration, the plasma Compound A1 concentration became lower immediately after the dialysis by 75-81% than that just before the dialysis.

Serum iPTH concentration: In the Compound A1-administered group, the serum iPTH concentration became lower than that just before the administration with a single administration, where the effect continued up to 66 hours after the administration (just before the dialysis). Here, the change in the serum iPTH concentration 66 hours after the administration was a percentage decrease of 27% in the 0.025 mg dose group, 48% in the 0.05 mg dose group, 44% in the 0.1 mg dose group, 57% in the 0.2 mg dose group, 78% in the 0.4 mg dose group, 69% in the 0.6 mg dose group, and 66% in the 0.8 mg dose group.

Safety: While relative vomiting and nausea were observed upon a single administration in the 0.4 mg and higher dose groups and in the 0.6 mg and higher dose groups, respectively, both were non-severe and mild events and no other clinical problem was observed.

(2) Repeated administration: 39 cases (Compound A1-administered group: 28 cases, and placebo group: 11 cases)

Pharmacokinetic evaluation: Compound A1 was present mainly as an unchanged substance in the plasma with repeated administration. Furthermore, since the trough concentration of Compound A1 was generally constant before the dialysis following the longest interval between the dialysis sessions, the trough concentration of Compound A1 in the plasma was found not to rise before the dialysis by the repeated administration. Thus, the medicinal composition of the present invention was found to be rapidly eliminated by dialysis and has not no accumulating property.

Serum iPTH concentration: In the Compound A1-administered group, the serum iPTH concentration decreased during the test period and thus Compound A1 maintained its effect with repeated administration. Here, the change in the serum iPTH concentration on Day 22 of the test (three days after the ninth Compound A1 administration) was a percentage decrease of 8% in the 0.05 mg dose group, 25% in the 0.1 mg dose group, and 36% in the 0.2 mg dose group.

Safety: Although decrease in the corrected Ca was observed in the 0.2 mg dose group and the 0.05 mg dose group with repeated administration, all of them were mild and none caused a problem significant to safety. Decrease in the corrected Ca was not observed in the 0.1 mg dose group.

From the above results, the medicinal composition of the present invention was found to be useful as an agent for preventing or treating secondary hyperparathyroidism with reduced side effects when used in Japanese adults with a daily dose in a range of 0.025 mg-0.8 mg.

INDUSTRIAL APPLICABILITY

The medicinal composition of the present invention is useful as an agent for preventing or treating secondary hyperparathyroidism under maintenance dialysis, and the like.

The invention claimed is:

1. A method for preventing or treating secondary hyperparathyroidism under maintenance dialysis, comprising administering to a subject in need thereof a composition comprising 3-{[(2 S)-2-amino-2-carboxyethyl]carbamoylamino}-5-chloro-4-methylbenzenesulfonic acid, a pharmaceutically acceptable salt thereof or a solvate thereof, wherein said composition is intravenously administered at the end of dialysis at a daily dose of 0.025 mg to 0.8 mg for an adult.

2. The method according to claim 1, wherein said medicinal composition is intravenously administered at a daily dose of 0.025 to 0.4 mg for an adult.

3. The method according to claim 1, wherein said medicinal composition is intravenously administered at the end of dialysis at a daily dose of 0.0.5 to 0.2 mg for and adult.

4. The method according to claim 1, wherein said end of dialysis means the end of each dialysis session in a dialysis schedule of 3 to 5 sessions a week.

5. The method according to claim 1 which comprises administering sodium 3-{[(2S)-2-amino-2-carboxyethyl]carbamoylamino}-5-chloro-4-methylbenzenesulfonate or a solvate thereof.

6. A method for preventing or treating secondary hyperparathyroidism under maintenance dialysis with reduced side effects, comprising administering to a subject in need thereof a composition comprising 3-{[(2S)-2-amino-2-carboxyethyl]-carbamoylamino}-5-chloro-4-methylbenzenesulfonic acid, a pharmaceutically acceptable salt thereof or a solvate thereof, wherein said composition is intravenously administered at the end of dialysis at a daily dose of 0.025 mg to 0.8 mg for an adult.

7. The method according to claim 6, wherein said medicinal composition is intravenously administered at a daily dose of 0.025 to 0.4 mg for an adult.

8. The method according to claim 6, wherein said medicinal composition is intravenously administered at the end of dialysis at a daily dose of 0.05 to 0.2 mg for and adult.

9. The method according to claim 6, wherein said end of dialysis means the end of each dialysis session in a dialysis schedule of 3 to 5 sessions a week.

10. The method according to claim 6, which comprises administering sodium 3-{[(2S)-2-amino-2-carboxyethyl]carbamoylamino}-5-chloro-4-methylbenzenesulfonate or a solvate thereof.

11. A method for preventing or treating secondary hyperparathyroidism under maintenance dialysis without manifesting significant accumulating property, comprising administering to a subject in need thereof a composition comprising 3-{[(2 S)-2-amino-2-carboxyethyl]carbamoylamino}-5-chloro-4-methylbenzenesulfonic acid, a pharmaceutically acceptable salt thereof or a solvate thereof, wherein said composition is intravenously administered at the end of dialysis at a daily dose of 0.025 mg to 0.8 mg for an adult.

12. The method according to claim 11, wherein said medicinal composition is intravenously administered at a daily dose of 0.025 to 0.4 mg for an adult.

13. The method according to claim 11, wherein said medicinal composition is intravenously administered at the end of dialysis at a daily dose of 0.05 to 0.2 mg for and adult.

14. The method according to claim 11, wherein said end of dialysis means the end of each dialysis session in a dialysis schedule of 3 to 5 sessions a week.

15. The method according to claim 11, which comprises administering sodium 3-{[(2S)-2-amino-2-carboxyethyl]carbamoylamino}-5-chloro-4-methylbenzenesulfonate or a solvate thereof.

* * * * *

UNITED STATES PATENT AND TRADEMARK OFFICE
CERTIFICATE OF CORRECTION

PATENT NO. : 11,311,508 B2
APPLICATION NO. : 16/954884
DATED : April 26, 2022
INVENTOR(S) : Daisuke Kataoka et al.

It is certified that error appears in the above-identified patent and that said Letters Patent is hereby corrected as shown below:

In the Claims

In Column 18, Claim 1, Line 33, delete "a composition" and insert -- a medicinal composition --, therefor.

In Column 18, Claim 1, Line 34, delete "3-{[(2 S)-2-amino-2-carboxyethyl]carbamoyl-" and insert -- 3-{[(2S)-2-amino-2-carboxyethyl]carbamoyl- --, therefor.

In Column 18, Claim 3, Line 45, delete "0.0.5 to 0.2 mg for and adult." and insert -- 0.05 to 0.2 mg for an adult. --, therefor.

In Column 18, Claim 6, Line 56, delete "a composition" and insert -- a medicinal composition --, therefor.

In Column 18, Claim 6, Line 59, delete "said composition" and insert -- said medicinal composition --, therefor.

In Column 18, Claim 8, Line 67, delete "and adult." and insert -- an adult. --, therefor.

In Column 19, Claim 11, Line 11, delete "a composition" and insert -- a medicinal composition --, therefor.

In Column 19, Claim 11, Line 12, delete "3-{[(2 S)-2-amino-2-carboxyethyl]carbamoyl-" and insert -- 3-{[(2S)-2-amino-2-carboxyethyl]carbamoyl- --, therefor.

In Column 19, Claim 11, Line 15, delete "said composition" and insert -- said medicinal composition --, therefor.

In Column 19, Claim 13, Line 23, delete "and adult." and insert -- an adult. --, therefor.

Signed and Sealed this
Fifteenth Day of July, 2025

Coke Morgan Stewart
*Acting Director of the United States Patent and Trademark Office*